United States Patent [19]

Shankland et al.

[11] Patent Number: 5,376,333

[45] Date of Patent: Dec. 27, 1994

[54] ETHYLENE OXIDE-CARRIER GAS COMPOSITIONS HAVING IMPROVED FLAMMABILITY SUPPRESSANT CHARACTERISTICS

[75] Inventors: Ian R. Shankland; David P. Wilson; Rajat S. Basu, all of Williamsville, N.Y.

[73] Assignee: AlliedSignal, Inc., Morristown, N.J.

[21] Appl. No.: 386,926

[22] Filed: Jul. 28, 1989

[51] Int. Cl.$^5$ .............................................. A01N 29/00
[52] U.S. Cl. ....................................... 422/34; 514/475; 514/743; 514/757; 570/134; 570/168
[58] Field of Search ................. 514/475, 743, 757; 422/34; 570/134, 168; 424/45

[56] References Cited

U.S. PATENT DOCUMENTS

| | | | |
|---|---|---|---|
| 2,891,838 | 6/1959 | Kaye | 422/34 |
| 3,068,064 | 12/1962 | McDonald | 422/34 |
| 3,169,906 | 2/1965 | Donchak et al. | 167/58 |
| 3,359,159 | 12/1967 | Fulton et al. | 167/39 |
| 3,589,861 | 6/1971 | Gunther | 422/25 |
| 4,174,295 | 11/1979 | Bargigia et al. | 424/45 |
| 4,954,284 | 9/1990 | Batt et al. | 252/170 |
| 4,976,922 | 12/1990 | Chippett et al. | 514/475 |
| 5,039,484 | 8/1991 | Chippett et al. | |

OTHER PUBLICATIONS

H. F. Coward & G. W. Jones, "Limits of Flammability of Gases and Vapors", Bulletin 503 Bureau of Mines.
R. Hirst, "Chemical Extinguishants" Inst. Fire Engr. Quarterly 25 (No. 59) pp. 231–250, Sep. 1965.
R. Ernst, "Ethylene Oxide Gaseous Sterilization for Industrial Applications", Ind. Sterilization Int'l. Symposium pp. 181–208 (1972).
J. J. Perkins, "Sterilization of Medical and Surgical Supplies with Ethylene Oxide", Principles and Methods of Sterilization, pp. 501.–529 (2d ed. 1969).
P. A. Sanders, "Principles of Aerosol Technology", pp. 140–157.
Aerosols, Sterilants and Miscellaneous Uses, Technical Options Reports, published Jun. 30, 1989. See, in particular pp. 26–41.

Primary Examiner—Lyle A. Alexander
Attorney, Agent, or Firm—Finnegan, Henderson, Farabow, Garrett & Dunner

[57] ABSTRACT

Compositions of ethylene oxide and monochlorotetrafluoroethane which are useful as sterilizing agents. These novel compositions are environmentally acceptable, possess improved flammability suppressant characteristics, and are capable of maintaining a greater ethylene oxide concentration than traditional sterilizing gas compositions.

36 Claims, No Drawings

ETHYLENE OXIDE-CARRIER GAS COMPOSITIONS HAVING IMPROVED FLAMMABILITY SUPPRESSANT CHARACTERISTICS

FIELD OF THE INVENTION

The invention relates to novel compositions of ethylene oxide and monochlorotetrafluoroethane having improved flammability suppressant characteristics. These compositions are useful in the gaseous sterilization of heat or moisture sensitive materials.

BACKGROUND OF THE INVENTION

Sterilization with a germicidal agent, such as ethylene oxide gas or ethylene oxide containing gas mixtures, has played an increasingly important role in sterilizing heat or moisture sensitive materials. Rapid growth in the use of sterile, disposable medical devices is just one consequence of gaseous sterilization with agents such as ethylene oxide. Gaseous sterilization of re-useable medical and surgical equipment using a nonflammable mixture of ethylene oxide and a carrier gas has also proven to be reliable, cost effective technology for many hospitals.

The basic gaseous sterilization process consists of evacuating the sterilization chamber containing articles to be sterilized, preconditioning the articles at an optimal relative humidity, generally between 20–70%, admitting the sterilizing gas at an appropriate pressure and temperature, maintaining contact between the sterilizing atmosphere and the articles to be sterilized for an appropriate time, and finally discharging and evacuating the chamber to remove the sterilant gas.

Although there are many variations on the basic process, the major factors which have to be controlled in order to effect the sterilization are exposure time, temperature, ethylene oxide pressure or partial pressure, and relative humidity. The following prior art references provide a good description of the standard sterilization processes and apparatus with which the gaseous sterilizing agents of the invention are useful: J. J. Perkins, Principles and Methods of Sterilization, at 501–530 (2d ed. 1969); and Ethylene Oxide Gaseous Sterilization For Industrial Applications, Industrial Sterilization International Symposium, 181–208 (1972), U.S. Pat. No. 3,068,064 and U.S. Pat. No. 3,589,861.

By itself, ethylene oxide is an extremely flammable gas. Its flammability range extends from about 3.0% by volume to 100% by volume in air. Thus, when ethylene oxide is used alone as a sterilizing gas, precautions such as explosion proof equipment are mandatory.

A preferable practice is to blend the ethylene oxide with another fluid which serves to dilute the ethylene oxide and render the mixture as a whole, nonflammable. Two such blends which have been used as sterilizing gases are dichlorodifluoromethane (CFC-12)/ethylene oxide and carbon dioxide/ethylene oxide. Inert carrier gases like CFC-12 and carbon dioxide inhibit the flammability of ethylene oxide and provide sufficient autogeneous vapor pressure to deliver the liquid mixture from the source cylinder to the heat exchanger of the sterilizer vessel where the liquid mixture is vaporized.

The CFC-12/ethylene oxide blend is generally supplied as a liquid mixture consisting of 88% by weight CFC-12 and 12% by weight ethylene oxide. This composition is below the critical flammability composition of about 14–15% by weight ethylene oxide in CFC-12, and is therefore nonflammable. A typical hospital sterilization process which utilizes the CFC-12/ethylene oxide blend is performed by evacuating the chamber containing the articles to about 20–24 inches of mercury vacuum, preconditioning the articles at an optimal relative humidity, and filling the chamber to about 10 psig pressure with the gas mixture. Sterilization is generally performed around 130° F. The 88/12 by weight CFC-12/ethylene oxide mixture produces a gas mixture containing 72.8 volume or mole percent CFC-12 and 27.2 volume or mole percent ethylene oxide. This composition provides about 630 milligrams of ethylene oxide per liter at the stated typical operating condition. The concentration (mg/liter) of ethylene oxide present in the sterilization chamber is critical in determining the required exposure time and ultimate sterilization efficiency. The Association for the Advancement of Medical Instrumentation (AAMI) recommends an absolute minimum ethylene oxide concentration of 450 mg/liter.

The nonflammable carbon dioxide/ethylene oxide blend is also supplied as a liquid mixture consisting of about 90% by weight carbon dioxide and about 10% by weight ethylene oxide. This blend produces a gas mixture containing 90% by volume or mole carbon dioxide and 10% by volume or mole ethylene oxide. The available ethylene oxide concentration (mole percent) is significantly less than that obtained from the 88/12 by weight CFC-12/ethylene oxide blend. Sterilization using carbon dioxide/ethylene oxide is generally performed at a greater pressure then that used with CFC-12/ethylene oxide to increase the concentration of ethylene oxide, or is performed for greater exposure time which decreases productivity.

A disadvantage of using CFC-12 in sterilant gas mixtures is that fully halogenated chlorofluorocarbons such as CFC-12 have been implicated in causing environmental problems. Specifically, CFC-12 has substantial potential for stratospheric ozone depletion and global warming.

Although the major purpose of the inert carrier gas component in these sterilizing gas mixtures is to mask the flammability characteristics of ethylene oxide, simple substitution of an arbitrary nonflammable gas does not necessarily ensure a useful sterilizing gas mixture. First, the flammability properties of the blend must be such that a sufficient amount of ethylene oxide (mg/liter at a typical pressure and temperature) is delivered by the blend to effect the sterilization in an appropriate time. If the carrier gas does not mask the flammability to a sufficient extent, a lower concentration of ethylene oxide must be used to ensure nonflammability. In such a case either a longer exposure time is required to perform the sterilization, which affects productivity, or greater operating pressures are required to increase the effective ethylene oxide density in the sterilization chamber. Increasing the operating pressure is generally not a viable alternative because existing sterilization chambers may not be rated for the increased pressure, and as pointed out by Gunther in U.S. Pat. No. 3,589,861, increased pressure can lead to swelling and rupture of the sealed plastic bags commonly used to package disposable medical devices. Indeed, lower operating pressures are advantageous in this respect. The need for a greater operating pressure or increased exposure time has limited the acceptance of the 90/10 carbon dioxide/ethylene oxide mixture in comparison to the 88/12 CFC-12/ethylene oxide mixture.

A candidate inert diluent or carrier gas must also be miscible with ethylene oxide in the liquid phase and must not segregate from the ethylene oxide to any great extent during vaporization. Segregation or fractionation can lead to potentially flammable or explosive situations. The degree of segregation that may occur during evaporation is related to the relative volatility of the components of the mixture. The vapor pressure of ethylene oxide at 70° F. is 22 psia while the vapor pressures of CFC-12 and carbon dioxide at 70° F. are 85 and 850 psia, respectively. The vapor pressure data indicate a very large difference in volatility between carbon dioxide and ethylene oxide, and hence a susceptibility for carbon dioxide/ethylene oxide blends to fractionate.

Kaye, in U.S. Pat. No. 2,891,838 discloses sterilizing compositions comprising ethylene oxide, CFC-12, and CFC-11 (trichlorofluoromethane). In this instance the ethylene oxide is blended with two other components, one which is more volatile (CFC-12) than ethylene oxide and the other which is less volatile (CFC-11) than ethylene oxide, reducing the potential for fractionation into the flammable region. This particular 3-component blend has not been widely accepted because of material compatibility problems, i.e., CFC-11 is incompatible with some plastic or polymeric materials.

Thus, the need exists for a carrier gas which is compatible with the objects being sterilized; chemically stable; environmentally acceptable; minimally segregating; contains at least 27 mole percent ethylene oxide; and provides sufficient vapor pressure to deliver the liquid mixture to the sterilization chamber.

Accordingly, it is an object of the invention to provide a novel sterilizing gas mixture containing ethylene oxide.

It is an object of the invention to provide such a sterilizing gas mixture which contains an inert fluorocarbon diluent, or diluents, which are considered to be environmentally acceptable.

Another object of the invention is to provide a nonflammable gas mixture which is capable of providing a gas phase concentration (mole percent or mg/liter) of ethylene oxide equivalent to or in excess of that concentration provided by 88/12 CFC-12/ethylene oxide.

It is another object of the invention to provide a sterilizing gas mixture which is miscible and minimally segregating.

Another object of the invention is to provide a sterilizing gas mixture with sufficient vapor pressure to deliver the liquid mixture to the sterilization chamber.

Still another object of this invention is to provide a sterilizing gas mixture which is compatible with plastic and polymers used in the construction of medical devices.

Other objects and advantages of the invention will become apparent from the following description of the invention.

SUMMARY OF THE INVENTION

The invention relates to compositions which are useful in gas sterilization processes. Specifically, the invention relates to novel sterilant gas compositions comprising effective amounts of monochlorotetrafluoroethane and ethylene oxide which are environmentally acceptable, possess improved flammability suppressant characteristics, and are capable of maintaining a greater ethylene oxide concentration than traditional sterilizing gas compositions.

DETAILED DESCRIPTION OF THE INVENTION

In accordance with the invention, novel compositions of ethylene oxide and monochlorotetrafluoroethane having improved flammability suppressant characteristics have been discovered.

Monochlorotetrafluoroethane exists in two isomeric forms, 1-chloro-1,2,2,2-tetrafluoroethane (HCFC-124) and 1-chloro-1,1,2,2-tetrafluoroethane (HCFC-124a). Each isomer exhibits the properties of the invention, i.e., environmental acceptability, minimal segregation, improved flammability suppressant characteristics, and the capacity to maintain higher ethylene oxide concentrations than traditional sterilizing gas compositions. Hence, monochlorotetrafluoroethane for purposes of this invention may consist of either isomer or an admixture of the isomers in any proportion. The preferred isomer is 1-chloro-1,2,2,2-tetrafluoroethane. Due to the close boiling points of 1-chloro-1,2,2,2-tetrafluoroethane ($-12.0°$ C.) and 1-chloro-1,1,2,2-tetrafluoroethane ($-10.2°$ C.), each of the above isomers when commercially produced may contain small amounts, perhaps up to 10 weight percent, of the other isomer. Thus, it is understood that the monochlorotetrafluoroethane described in this invention preferably refers to an admixture of HCFC-124/HCFC-124a; containing up to about 10 weight percent HCFC-124a.

Since monochlorotetrafluoroethane is not perhalogenated, it is considered to be environmentally acceptable; having a lower potential for stratospheric ozone depletion and global warming than fully halogenated chlorofluorocarbons. Atmospheric models indicate that HCFC-124 has a much lower atmospheric lifetime than CFC-12 and, as a consequence, it has an estimated ozone depletion potential 50 times lower than that of CFC-12 and an estimated global warming potential 30 times lower than CFC-12.

The vapor or gas mixtures arising from the blends of monochlorotetrafluoroethane and ethylene oxide are nonflammable and contain more ethylene oxide on a mole percent or mg/liter basis than the traditional 88/12 CFC-12/ethylene oxide sterilizing gas mixture. The greater concentration of ethylene oxide available in the nonflammable monochlorotetrafluoroethane blends is a surprising result since one would normally expect CFC-12 to exhibit greater flammability suppressant properties than monochlorotetrafluoroethane.

The nonflammable monochlorotetrafluoroethane/ethylene oxide compositions of the invention comprise from about 3.0 to about 13.0 weight percent ethylene oxide and from about 97.0 to about 87.0 weight percent monochlorotetrafluoroethane.

With respect to the preferred embodiment of the invention, the composition which provides about 27.7 mole percent ethylene oxide in monochlorotetrafluoroethane, i.e., the composition comprising from about 9.0 to about 12.0 weight percent ethylene oxide and from about 91.0 to about 88.0 weight percent monochlorotetrafluoroethane, is optimal.

In another embodiment of the invention, additional nonflammable, more volatile, inert components may be added to increase the vapor pressure of the mixture. Illustrative suitable components include chlorodifluoromethane (HCFC-22), 1,2,2,2-tetrafluoroethane (HFC-134a), 1,1,2,2-tetrafluoroethane (HFC 134), pentafluoroethane (HFC-125), nitrogen, carbon dioxide, and sulfur hexafluoride. Other suitable volatile components will readily occur to those skilled in the art. Compositions incorporating these components comprise from about 9.0–12.0 weight percent ethylene oxide, from about 63.0 to about 85.0 weight percent monochlorotetrafluoroethane, and from about 27.0 to about 3.0 weight percent of a more volatile, nonflammable, inert component chlorodifluoromethane, 1,2,2,2-tetrafluoroethane, 1,1,2,2-tetrafluoroethane, pentafluoroethane, nitrogen, carbon dioxide, and sulfur hexafluoride.

Ethylene oxide has a flash point less than −20° F., and forms explosive mixtures in air from about 3.0 volume percent to 100 volume percent ethylene oxide. The addition of a chemically inert vapor or gas decreases the flammability of the ethylene oxide/air mixture. With the addition of a sufficient inert component, the blend is rendered nonflammable. If the inert component is truly inert, i.e., does not participate chemically in the combustion process, then the extinctive efficiency of the inert species depends on such physical properties as its specific heat and thermal conductivity. See, e.g., U.S. Bureau of Mines, Bull. No. 503, Limits of Flammability of Gases and Vapors, 5 (1952). The physical extinction mechanism relies upon removal of the energy required to maintain combustion.

The flammability properties of ethylene oxide/halocarbon blends do not follow this simple physical correlation (as is shown in Example 1); rather, it is well known that their extinctive properties stem from a chemical mechanism whereby the halogen species chemically participates in the combustion reaction, and interferes with or inhibits the combustion reaction. In his article, Chemical Extinguishants, 25 Institution Of Fire Engineers Quarterly 231–250 (2d ed. 1965), R. Hirst states that the extinguishing ability of halogen species follows the order I>Br>Cl>F. Iodine containing halocarbons are generally known to be less chemically stable and more toxic than other members of the halocarbon family. The bromine containing species are known to possess a much greater ozone depletion potential than their chlorine containing analogue. Thus, for environmental reasons, potential halocarbon carrier gases are restricted to the hydrohalocarbons containing fluorine and/or chlorine. A hydro-substituted halocarbon possesses a much lower atmospheric lifetime than fully halogenated chlorofluorocarbons. However, decreasing the halogen content of the carrier gas, by incorporating hydrogen in the molecule, tends to reduce the flammability suppressant or extinctive properties of the carrier gas. Example 1 below shows that the hydro-substituted halocarbon, monochlorotetrafluoroethane, possesses surprisingly improved flammability suppressant properties in comparison to the fully halogenated CFC-12.

In the process embodiment of the invention, the compositions comprising monochlorotetrafluoroethane and ethylene oxide may be used as sterilizing gases in any manner well known in the art by essentially exposing the articles to be sterilized to the sterilizing gas under conditions and for a period of time necessary to achieve the desired degree of sterility. Typically, the process is effected by placing the articles to be sterilized in a chamber, evacuating the chamber, humidifying the chamber, and exposing the articles to the sterilizing gas for an appropriate period of time.

The monochlorotetrafluoroethane employed in the following examples is essentially pure HCFC-124, i.e., 99.5 weight percent HCFC-124.

EXAMPLE 1

This example shows by means of vapor phase flammability measurements for various ethylene oxide/carrier gas mixtures in air, that HCFC-124 surprisingly suppresses the flammability of ethylene oxide to a greater extent than CFC-12.

Flammability measurements were performed using a method based on the ASTM E-681 method prescribed for measuring the flame limits of vapors in air. The ASTM E-681 method involves preparing a gas phase mixture of ethylene oxide, carrier gas, and air in a 5 liter spherical vessel. Once the components have been adequately mixed, the gas mixture is ignited at the center of the vessel. If a flame propagates away from the ignition source, then the gas mixture is deemed flammable. The extent of flame propagation necessary for the mixture to be classified as flammable is defined in the ASTM E-681 method definition.

Gas mixtures were prepared by evacuating the vessel and admitting the carrier gas, ethylene oxide, and air and measuring the pressure after each addition. The composition of the blend is determined from the component partial pressures. A uniform composition is ensured by stirring the mixture with a magnetically driven propeller.

Three different ignition sources were employed to determine the flammability characteristics of the carrier gas/ethylene oxide blends. One ignition source consisted of a 45 Joule, 0.1 second duration electric spark discharged between two electrodes placed at the center of the vessel. The second ignition source is termed a fused or exploding wire and consists of a 0.75 inch, 40 gauge copper wire soldered between two heavy gauge electrical conductors. Switching the 110V, 60 Hz mains electrical supply causes the wire to increase in temperature very rapidly, the wire vaporizes almost instantaneously. The third ignition source consists of a kitchen match head held in a coil of nichrome wire. Heating the wire electrically causes the match to ignite.

By preparing various compositions of ethylene oxide and carrier gas in air and determining their flammability, it is possible to map out the region of compositions in air which are flammable. See, e.g., P. A. Sanders, The Handbook of Aerosol Technology at 146 (2d ed. 1979) The maximum amount of ethylene oxide which can be blended with the carrier gas, and remain nonflammable in all proportions in air, can be determined from such a plot. Table I summarizes the maximum or critical composition of ethylene oxide attainable with both CFC-12 and HCFC-124.

TABLE I

| Carrier Gas | Maximum ethylene oxide composition (mole or volume percent) | Ignition Source |
| --- | --- | --- |
| HCFC-124 | 30.3 | 45 J/0.1 sec spark |
| CFC-12 | 28.7 | 45 J/0.1 sec spark |
| HCFC-124 | 27.2 | Exploding wire |
| CFC-12 | 26.9 | Exploding wire |
| HCFC-124 | 24.6 | Heated wire/match |
| CFC-12 | 22.6 | Heated wire/match |

This data indicates that for each ignition source, a greater mole or volume percent ethylene oxide is attainable in a nonflammable HCFC-124 blend. Up to 9% more ethylene oxide is provided for sterilization by using the HCFC-124 carrier gas, thus providing a more effective or more rapid sterilization process.

EXAMPLE 2

This example shows that nonflammable HCFC-124/ethylene oxide blends unexpectedly contain more ethylene oxide than CFC-12.

Flammability measurements were performed for various fluorocarbon/ethylene oxide blends using the method outlined in the previous example. In this case the heated wire/match ignition source was employed.

Flammability measurements were performed for ethylene oxide blends with HFC-134a and HCFC-22 in addition to HCFC-124 and CFC-12. HFC-134a and HCFC-22 are also regarded as more environmentally acceptable fluorocarbons, in fact, HFC-134a has been suggested as an alternative for CFC-12 in certain air conditioning and refrigeration applications, and HCFC-22 is already produced commercially. These fluorocarbons possess different properties than HCFC-124 and are included for the sake of the comparison.

Table II lists the critical ethylene oxide concentration as well as some of the physical and. molecular properties of the fluorocarbon diluents. fluorocarbons, in fact, HFC-134a has been suggested as an alternative for CFC-12 in certain air conditioning and refrigeration applications, and HCFC-22 is already produced commercially. These fluorocarbons possess different properties than HCFC-124 and are included for the sake of the comparison.

TABLE II

|  | CFC-12 | HCFC-124 | HCFC-22 | HFC-134a |
|---|---|---|---|---|
| Max. ethylene oxide (vol. %) | 22.6 | 24.6 | 11.3 | 12.8 |
| Specific Heat @ 27° C. (J/mol/K) | 72.7 | 98.5 | 56.1 | 87.2 |
| Halogen Content Of Diluents |  |  |  |  |
| Wt. % Chlorine | 58.6 | 26.0 | 41.0 | 0.0 |
| Wt. % Fluorine | 31.4 | 55.7 | 44.0 | 74.5 |
| Wt. % Halogen | 90.0 | 81.7 | 85.0 | 74.5 |
| Mole % Chlorine | 40.0 | 12.5 | 20.0 | 0.0 |
| Mole % Fluorine | 40.0 | 50.0 | 40.0 | 50.0 |
| Mole % Halogen | 80.0 | 62.5 | 60.0 | 50.0 |

This table shows that the flammability suppressant properties of these potential carrier gases do not follow the heat capacity trend nor do they follow the trend of halogen content. Based on hydrogen and halogen content, one would expect the following pattern of flammability suppressant behavior; CFC-12>HCFC-124>,HCFC-22>HFC-134a. However, the data listed in Tables I and II show that HCFC-124 is the best flammability suppressant for ethylene oxide; the trend being HCFC-124>CFC-12>HFC-134a>HCFC-22.

EXAMPLE 3

Vapor pressures of mixtures of ethylene oxide with HCFC-124 and mixtures of ethylene oxide, HCFC-124 and HCFC-22 were measured. Nonflammable HCFC-124/ethylene oxide blends possess vapor pressures greater than 1 atmosphere which is sufficient to expel the liquid mixture from a source cylinder to the evacuated or partially evacuated sterilizer chamber. Addition of a more volatile component, such as HCFC-22, to the HCFC-124/ethylene oxide mixture increases the vapor pressure of the blend, but with some reduction inflammability suppressant properties. Increased vapor pressure may sometimes be necessary to provide sufficient liquid flow from the cylinder, especially if the delivery lines are long.

Vapor pressures were measured using a calibrated Bourdon gauge accurate to ±1%. Mixtures were prepared gravimetrically and allowed to reach thermal equilibrium in a temperature controlled water bath before determining the vapor pressure.

TABLE III

| Blend Composition | | | Vapor Pressure (psia) | |
|---|---|---|---|---|
| wt. % HCFC-124 | wt. % HCFC-22 | wt. % ethylene oxide | @ 70° F. | @ 130° F. |
| 90.0 | 0.0 | 10.0 | 38.2 | 98.7 |
| 72.0 | 18.0 | 10.0 | 55.7 | 133.3 |
| 63.0 | 27.0 | 10.0 | 64.2 | 150.6 |

Addition of the more volatile HCFC-22 increases the vapor pressure of the mixtures as shown in Table III. Other more volatile diluents such as HFC-134a, HFC-134, HFC-125, sulfur hexafluoride, carbon dioxide and nitrogen have a similar effect. These diluents will decrease to some extent the flammability suppressant properties of HCFC-124. For example, a 70/30 blend of HCFC-124 and HCFC-22 when blended ethylene oxide will remain nonflammable at compositions up to about 23.3 vol. % ethylene oxide. Certain HCFC-124/volatile diluent compositions exhibit better flammability suppressant properties than the fully halogenated CFC-12. For example, HCFC-124/HCFC-22 compositions containing less than 20 weight percent HCFC-22 exhibit better flammability suppressant properties than CFC-12.

If a greater vapor pressure than that attainable with nonflammable blends of HCFC-124/ethylene oxide is required, and the reduction in ethylene oxide content which follows from including a more volatile diluent such is HCFC-22 is unacceptable, then another approach should be utilized. For example, the headspace of the HCFC-124/ethylene oxide cylinder could be pressurized with an inert gas such as nitrogen, or the cylinder could be warmed, e.g., increasing the temperature to 130° F. increases the vapor pressure of a 90/10 HCFC-124/ethylene oxide blend from 38.2 to 98.7 psia.

EXAMPLE 4

This example shows that HCFC-124 like CFC-12 is compatible with plastics and polymers commonly used in the construction of medical devices.

Compatibility tests were performed by expressing the test material to the fluorocarbon vapor at 24.7 psia and 130° F. for 16 hours. At the end of the exposure period any change in weight of the part was determined and a visual inspection performed.

TABLE IV

|  | % Wt. Change After Exposure | |
|---|---|---|
|  | CFC-12 | HCFC-124 |
| Polypropylene/Lexan | 0.0 | −0.1 |
| Polycarbonate/Lexan | 0.8 | 0.7 |
| Polystyrene | 0.8 | 1.4 |
| Polypropylene | 1.1 | 0.6 |
| Latex/Silicone Rubber | 2.6 | 2.1 |
| PVC | 0.1 | 1.0 |
| Cotton Gauze | −2.3 | −0.9 |
| Synthetic Skin | −1.0 | −0.2 |

The data summarized in Table IV indicate essentially no difference in compatibility properties between CFC-12 and HCFC-124. Those plastics such as polycarbonate and polystyrene which are incompatible with certain fluorocarbons, show no deleterious effect when exposed to HCFC-124.

EXAMPLES 5-6

The flammability suppressant properties of HCFC-124a and 90:10 HCFC-124/124a are studied by repeating the experiment outlined in Example 1. The results obtained are substantially the same as those for HCFC-124, i.e., HCFC-124a and 90:10 HCFC-124/124a each suppresses the flammability of ethylene oxide to a greater extent than does CFC-12.

EXAMPLES 7-8

In accordance with Example 2, the ethylene oxide concentration is monitored for various blends of HCFC-124a/ethylene oxide and 90:10 HCFC-124/124a/ethylene oxide. The results obtained are substantially the same as those for HCFC-124, i.e., non-flammable HCFC-124/ethylene oxide blends and nonflammable 90:10 HCFC-124/124a/ethylene oxide blends contain more ethylene oxide than CFC-12/ethylene oxide blends.

EXAMPLES 9-10

Vapor pressures of mixtures of HCFC-124a/ethylene oxide and 90:10 HCFC-124/124a/ethylene oxide are measured according to the procedure outlined in Example 3. The results obtained are substantially the same as those for HCFC-124, i.e., nonflammable HCFC-124a/ethylene oxide blends and nonflammable 90:10 HCFC-124/124a/ethylene oxide blends possess vapor pressures sufficient to expel the liquid mixture from a source cylinder to the evacuated or partially evacuated sterilizer chamber.

EXAMPLES 11-12

In accordance with the method of Example 4, the compatibility of HCFC-124a and 90:10 HCFC-124/124a with plastics and polymers commonly used in the construction of medical devices is studied. The results obtained are substantially the same as those for HCFC-124, i.e., there is essentially no difference in compatibility properties between CFC-12 and HCFC-124a and between CFC-12 and 90:10 HCFC-124/124a.

What is claimed:

1. A sterilizing gas composition comprising from about 97.0 to about 87.0 weight percent monochlorotetrafluoroethane and from about 3.0 to about 13.0 weight percent ethylene oxide.

2. The sterilizing gas composition of claim 1 wherein the monochlorotetrafluoroethane is 1-chloro-1,2,2,2-tetrafluoroethane.

3. The sterilizing gas composition of claim 1 wherein the monochlorotetrafluoroethane is 1-chloro-1,1,2,2-tetrafluoroethane.

4. A method of sterilizing articles comprising exposing the articles to an effective amount of the sterilizing gas composition of claim 1 under conditions and for a period of time necessary to achieve the desired degree of sterility.

5. A sterilizing gas composition of claim 1 wherein the said composition comprises from about 91.0 to about 89.0 weight percent monochlorotetrafluoroethane and from about 9.0 to about 11.0 weight percent ethylene oxide.

6. A method of sterilizing articles comprising exposing the articles to an effective amount of the sterilizing gas composition of claim 5 under conditions and for a period of time necessary to achieve the desired degree of sterility.

7. A sterilizing gas composition consisting essentially of from about 97.0 to about 87.0 weight percent monochlorotetrafluoroethane and from about 3.0 to about 13.0 weight percent ethylene oxide.

8. A method of sterilizing articles comprising exposing the articles to an effective amount of the sterilizing gas composition of claim 7 under conditions and for a period of time necessary to achieve the desired degree of sterility.

9. A sterilizing gas composition of claim 7 wherein said composition consists essentially of from about 91.0 to about 89.0 weight percent monochlorotetrafluoroethane and from about 9.0 to about 11.0 weight percent ethylene oxide.

10. A method of sterilizing articles comprising exposing the articles to an effective amount of the sterilizing gas composition of claim 9 under conditions and for a period of time necessary to achieve the desired degree of sterility.

11. The sterilizing gas composition of claim 1 wherein said composition further comprises a nonflammable, inert component which is more volatile than the mixture and capable of increasing the vapor pressure of the mixture.

12. A sterilizing gas composition of claim 11 wherein said more volatile, nonflammable, inert component is selected from the group consisting of chlorodifluoromethane, 1,2,2,2-tetrafluoroethane, 1,1,2,2-tetrafluoroethane, pentafluoroethane, nitrogen, carbon dioxide, and sulfur hexafluoride.

13. A sterilizing gas composition of claim 12 wherein said composition comprises from about 63.0 to about 85.0 weight percent monochlorotetrafluoroethane, about 10.0 weight percent ethylene oxide, and from about 27.0 to about 5.0 weight percent of the more volatile, nonflammable, inert component capable of increasing the vapor pressure of the mixture.

14. The sterilizing gas composition of claim 3 wherein the monochlorotetrafluoroethane is 1-chloro-1,2,2,2-tetrafluoroethane.

15. The sterilizing gas composition of claim 13 wherein the monochlorotetrafluoroethane is 1-chloro-1,1,2,2-tetrafluoroethane.

16. The sterilizing gas composition of claim 13 wherein the monochlorotetrafluoroethane is a mixture of 1-chloro-1,2,2,2-tetrafluoroethane and 1-chloro1,1,2,2-tetrafluoroethane containing up to about ten weight percent of 1-chloro-1,1,2,2-tetrafluoroethane.

17. A sterilizing gas composition comprising effective amounts of monochlorotetrafluoroethane and ethylene oxide.

18. A method of sterilizing articles comprising exposing the articles to the sterilizing gas composition of claim 17 under conditions and for a period of time necessary to achieve the desired degree of sterility.

19. A method for sterilizing an article comprising contacting the article with an effective amount of a sterilant mixture comprising from 8.7 to 31.6 mole percent ethylene oxide and from 68.4 to 91.3 mole percent 1-chloro-1,2,2,2-tetrafluoroethane.

20. The method of claim 19 wherein the sterilant mixture further comprises chlorodifluoromethane.

21. The method of claim 19 wherein the sterilant mixture further comprises nitrogen.

22. The method of claim 19 wherein the sterilant mixture is in gaseous form when it contacts the article.

23. The method of claim 19 wherein the ethylene oxide concentration is not more than 24.6 mole percent and the sterilant mixture is not flammable in any concentration of air.

24. The method of claim 19 wherein the sterilant mixture has a concentration of ethylene oxide of from 23.5 to 29.7 mole percent.

25. The method of claim 24 wherein the 1-chloro-1,2,2,2tetrafluoroethane has a concentration of from 70.3 to 76.5 mole percent.

26. A method for sterilizing an article comprising contacting the article with an effective amount of a sterilant mixture comprising from about 9.0 to about 12.0 weight percent ethylene oxide, from about 63.0 to about 85.0 weight percent 1-chloro1,2,2,2-tetrafluoroethane, and from about 3.0 to about 27.0 weight percent chlorodifluoromethane.

27. A method for sterilizing articles comprising exposing the articles to an effective amount of a nonflammable sterilizing gas composition comprising:
   (1) ethylene oxide in an amount sufficient to effect sterilization and monochlorotetrafluoroethane in an amount sufficient to render the composition nonflammable in air; or
   (2) ethylene oxide in an amount sufficient to effect sterilization and (a) monochlorotetrafluoroethane and (b) chlorodifluoromethane in amounts sufficient to render the composition nonflammable in air.

28. A sterilant mixture comprising from 8.7 to 31.6 mole percent ethylene oxide and from 68.4 to 91.3 mole percent 1-chloro-1,2,2,2-tetrafluoroethane.

29. The sterilant mixture of claim 28 further comprising chlorodifluoromethane.

30. The sterilant mixture of claim 28 further comprising nitrogen.

31. The sterilant mixture of claim 28 wherein the sterilant mixture is in gaseous form.

32. The sterilant mixture of claim 28 wherein the ethylene oxide concentration is not more than 24.6 mole percent and the sterilant mixture is not flammable in any concentration of air.

33. The sterilant mixture of claim 28 wherein the ethylene oxide has a concentration of from 23.5 to 29.7 mole percent.

34. The sterilant mixture of claim 33 wherein the 1-chloro1,2,2,2-tetrafluoroethane has a concentration of from 70.3 to 76.5 mole percent.

35. A sterilant mixture comprising from about 9.0 to about 12.0 weight percent ethylene oxide, from about 63.0 to about 85.0 weight percent 1-chloro-1,2,2,2-tetrafluoroethane, and from about 3.0 to about 27.0 weight percent chlorodifluoromethane.

36. A nonflammable sterilizing gas composition comprising:
   (1) ethylene oxide in an amount sufficient to effect sterilization and monochlorotetrafluoroethane in an amount sufficient to render the composition nonflammable in air; or
   (2) ethylene oxide in an amount sufficient to effect sterilization and (a) monochlorotetrafluoroethane and (b) chlorodifluoromethane in amounts sufficient to render the composition nonflammable in air.

* * * * *

UNITED STATES PATENT AND TRADEMARK OFFICE
CERTIFICATE OF CORRECTION

PATENT NO. : 5,376,333
DATED : December 27, 1994
INVENTOR(S) : Shankland et al.

It is certified that error appears in the above-indentified patent and that said Letters Patent is hereby corrected as shown below:

Col. 2, line 30, change "then" to --than--.

Col. 5, line 7, after "component" insert --e.g.,--.

Col. 6, line 45, after (2d ed. 1979) insert --.--.

Col. 7, line 21, delete "." after "and".

line 22, change "diluents. fluorocarbons" to --diluents. Fluorocarbons--.

Claim 14, column 10, line 43, "claim 3" should read --claim 13--.

Claim 16, column 10, line 52, "chloro1,1,2,2-tetrafluoroethane" should read --chloro-1,1,2,2-tetrafluoroethane--.

Claim 25, column 11, line 14, "1,2,2,2tetrafluoroethane" should read --1,2,2,2-tetrafluoroethane--.

UNITED STATES PATENT AND TRADEMARK OFFICE
CERTIFICATE OF CORRECTION

PATENT NO. : 5,376,333
DATED : December 27, 1994
INVENTOR(S) : Shankland et al.

It is certified that error appears in the above-indentified patent and that said Letters Patent is hereby corrected as shown below:

Claim 26, column 11, lines 21-22, "1-chloro1,2,2,2-tetrafluoroethane" should read --1-chloro-1,2,2,2-tetrafluoroethane--.

Claim 34, column 12, line 18, "1-chloro1,2,2,2-tetrafluoroethane" should read --1-chloro-1,2,2,2-tetrafluoroethane--.

Signed and Sealed this

Sixth Day of June, 1995

Attest:

BRUCE LEHMAN

*Attesting Officer*  *Commissioner of Patents and Trademarks*